United States Patent [19]

Kawahara et al.

[11] 4,308,014

[45] Dec. 29, 1981

[54] BONDING COMPOSITIONS TO THE HARD TISSUE OF HUMAN BODY

[75] Inventors: Haruyuki Kawahara, Moriguchi; Takashi Funakoshi, Osaka; Shozo Kudo, Minoo; Teruo Makita, Kobe, all of Japan

[73] Assignee: Kanebo Ltd., Tokyo, Japan

[21] Appl. No.: 138,815

[22] Filed: Apr. 9, 1980

[30] Foreign Application Priority Data

Apr. 11, 1979 [JP] Japan .................................. 54-44751

[51] Int. Cl.$^3$ ........................... C09K 3/10; C09K 3/34
[52] U.S. Cl. ..................................... 433/228; 106/35; 260/998.11; 433/217; 526/241; 526/273; 526/278; 526/279; 526/304; 526/318
[58] Field of Search ............... 526/241, 273, 278, 279, 526/304, 318; 260/998.11; 433/228, 217; 106/35

[56] References Cited

U.S. PATENT DOCUMENTS

| | | | |
|---|---|---|---|
| 2,865,899 | 12/1958 | Hurwitz | 526/279 |
| 3,542,585 | 11/1970 | Heit | 526/279 |
| 3,951,893 | 4/1976 | Gander | 526/318 |
| 4,147,688 | 4/1979 | Makhlouf et al. | 526/279 |

*Primary Examiner*—Stanford M. Levin
*Attorney, Agent, or Firm*—Blanchard, Flynn, Thiel, Boutell & Tanis

[57] ABSTRACT

Bonding compositions for the hard tissue of the human body comprising, as the main component, (A) at least one member of polymerizable acrylate esters, methacrylate esters, acrylamide derivatives or methacrylamide derivatives possessing at least one group selected from the group consisting of a carboxyl group, epoxy group, amino group and hydroxyl group, and (B) at least one member of alkoxy-containing titanium compounds or alkoxy-containing silicon compounds.

15 Claims, No Drawings

BONDING COMPOSITIONS TO THE HARD TISSUE OF HUMAN BODY

The present invention relates to a bonding composition capable of bonding to the hard tissue of the human body and more particularly, to a bonding agent for medical or dental use capable of bonding to the hard tissue of the human body, such as bones and teeth.

Conventionally silver amalgam, such as an amalgam of silver alloy and mercury, and silicate cement have been used as restorative filling materials. The dental amalgam is excellent in physical properties, but it shows low bonding to teeth and it is insufficient in impact resistance, which tends to cause recurrent caries because of insufficient sealing of the margins of a filling to a tooth and in addition, entails the fear of exerting adverse influences on the human body from the viewpoint of toxicity. Further, silicate cement has a solubility and in addition, likewise it is low in bonding to teeth and is insufficient in marginal sealing. Moreover, it entails such shortcomings as intense pulpal irritation. Epoxy type resin-based filling material has been used, but it entails such drawbacks as inferiority in hardness and abrasion resistance and it is high in the water sorption.

Compositions consisting predominantly of bisphenol A-diglycidylmethacrylate (hereinafter called "Bis-GMA" for short) which is better in the compressive strength and water resistance than prior materials and is comparatively low in the pulpal irritation, and a great deal of inorganic filler and containing, as polymerization catalyst, a benzoylperoxide-tertiary amine catalyst (hereinafter called the composite resin for short) as disclosed in the U.S. Pat. Nos. 3,539,533; 3,066,112, 3,926,906, etc., for instance, came to be used as a restorative filling material for anterior teeth, in particular. But, for the reasons that in addition to the somewhat insufficient bonding of Bis-GMA, notwithstanding that a hydrophilic group-containing Bis-GMA is used, the joint use of a great deal of inorganic filler enhances the viscosity of the composite resin and worsens the wetting on the tooth surface, that composition has the serious shortcomings that it is poor in the bonding to dentin and enamel, which causes shedding of the filling material after filling the tooth and induces recurrent caries because it does not give a good marginal seal.

Further, proposals have recently been made of methods for using bonding agents consisting predominantly of Bis-GMA, but not containing the inorganic filler, for the improvement of the bonding of the Bis-GMA type composite resin, but their effect is not as yet fully recognized.

Other than that, developments have been made of adhesives consisting predominantly of α-cyanoacrylate as a pit and fissure sealant or as an adhesive for orthodontics, but under the wet conditions that exist in the oral cavity, the bonding strength is lowered in a short period of time.

As mentioned above, no discovery has been made, up to the present time, of a bonding material having sufficient bonding strength to the hard tissue of the human body and, in addition, is capable of maintaining the bonding strength for a long time under such wet and temperature gradient-rich environments as in the oral cavity.

In view of such problems, the instant inventors studied bonding agents having excellent bonding strength to the hard tissue of the human body which led to the accomplishment of the present invention.

The present invention is designed to provide a bonding material having a steadfast and durable bonding strength to the hard tissue of the human body.

Another purpose of the present invention is to provide an excellent bonding material which exhibits a steadfast and durable bonding strength for bonding operative dentistry and prosthetic dentistry material to the hard tissue of the human body, such as dental composite resin, and the hard tissue of the human body, without losing the characteristics of the operative dentistry and prosthetic dentistry material.

Still other purposes and merits of the present invention will be clear from the explanations which follow:

According to the present invention, the said purposes and merits of the present invention can be achieved by bonding compositions capable of bonding to the hard tissue of the human body consisting predominantly of a composition comprising (A) 50–99.5% by weight of polymerizable acrylate esters, methacrylate esters, acrylamide derivatives or methacrylamide derivatives (hereinafter called the component A for short) possessing at least one group selected from the group consisting of carboxyl groups, epoxy group, amino group and hydroxyl group and (B) 0.5–50% by weight of at least one organic metal compound selected from the group consisting of alkoxy-containing titanium compounds and silicon compounds (hereinafter called the component B for short).

For the said acrylate esters or methacrylate esters used as the component A in the present invention any ones will do only if they possess at least one member selected from the group consisting of carboxyl group, epoxy group, amino group and hydroxyl group, but particularly preferred are those which are represented by following formula (1):

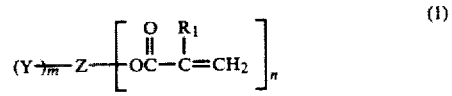

wherein
n is a positive integer of 1–3,
m is 1 or 2,

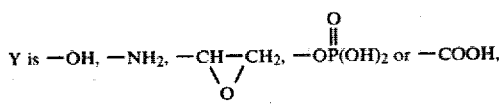

Z is a $C_{1-25}$ organic group of (n+m) valence and
$R_1$ is a hydrogen atom or a methyl group.
In the said group Y endows the acrylate esters or methacrylate esters with hydrophilic property.

A-I. The following are more preferred examples of such acrylate esters and methacrylate esters.

(1) Compounds represented by following formula (1-A):

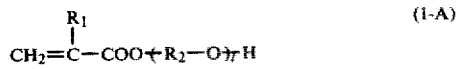

wherein
$R_1$ is a hydrogen atom or a methyl group, $R_2$ is a straight chain or branched $C_{2-6}$ aliphatic hydrocarbon residue optionally substituted with a hydroxyl group and being represented by $$-CH_2-CH_2-,\quad -\overset{CH_3}{\underset{|}{CH}}CH_2-\text{ or }-CH_2-\underset{\underset{OH}{|}}{CH}-CH_2-$$

and l is 1, 2 or 3.

(2) Phosphate esters of compounds of said formula (1-A) as represented by following formula (1-B):

$$CH_2=\overset{R_1}{\underset{|}{C}}-COO-R_2-\overset{O}{\underset{}{\overset{\|}{OP}}}(OH)_2 \qquad (1\text{-}B)$$

wherein $R_1$ and $R_2$ are as defined in the formula 1-A provided that when group $-R_2-$ possesses $-OH$ as substituent, this $-OH$ may be a phosphate ester.

(3) Compounds represented by following formula (1-C) and their phosphate esters:

$$CH_2=\overset{R_1}{\underset{|}{C}}-COO(CH_2\underset{\underset{OH}{|}}{CH}CH_2)_l O-R_3 \qquad (1\text{-}C)$$

wherein l and $R_1$ are as defined in the formula 1-A and $R_3$ is a $C_{1-3}$ alkyl or phenyl group.

(4) Compounds represented by following formula (1-D):

$$CH_2=\overset{R_1}{\underset{|}{C}}-COO-E-\underset{\phantom{X}}{\bigcirc}-X-\underset{\phantom{X}}{\bigcirc}-E-OOC-\overset{R_1}{\underset{|}{C}}=CH_2 \qquad (1\text{-}D)$$

wherein $R_1$ is as defined in the formula 1-A,

X is an alkylidene group such as $$-\underset{\underset{CH_3}{|}}{\overset{\overset{CH_3}{|}}{C}}-$$

or $-SO_2-$ and

E is a $C_{2-5}$ oxyalkylene group having a hydroxyl ($-OH$) group as a substituent or an alkylidene group containing between 1 and s carbon atoms with a hydroxyl group as a substituent.

(5) Compounds represented by following formula (1-E):

$$CH_2=\overset{R_1}{\underset{|}{C}}-COOCH_2\underset{\underset{OH}{|}}{CH}CH_2O-R'-OCH_2\underset{\underset{OH}{|}}{CH}CH_2OOC-\overset{R_1}{\underset{|}{C}}=CH_2 \qquad (1\text{-}E)$$

wherein R' is $-CH_2CH_2-,\ -CH_2CH_2OCH_2CH_2-,$ $$-\overset{\overset{CH_3}{|}}{CH}-CH_2-\text{ or }-\overset{\overset{CH_3}{|}}{CH}CH_2-O-\overset{\overset{CH_3}{|}}{CH}CH_2-$$

(6) Compounds represented by following formula (1-F):

$$\begin{array}{l} CH_2O\overset{O}{\overset{\|}{C}}-\overset{R_1}{\underset{|}{C}}=CH_2 \\ | \\ HOCH_2-C-CH_2O\overset{O}{\overset{\|}{C}}-\overset{R_1}{\underset{|}{C}}=CH_2 \\ | \\ CH_2O\overset{}{\underset{\underset{O}{\|}}{C}}-\overset{}{\underset{\underset{R_1}{|}}{C}}=CH_2 \end{array} \qquad (1\text{-}F)$$

wherein $R_1$ is as defined in the formula 1-A.

(7) Compounds represented by following formula (1-G):

$$CH_2=\overset{R_1}{\underset{|}{C}}-COO-R_2-NH_2 \qquad (1\text{-}G)$$

wherein $R_2$ is as defined in the formula 1-A.

(8) Compounds represented by following formula (1-H):

$$CH_2=\overset{R_1}{\underset{|}{C}}-COO(CH_2\underset{\underset{OH}{|}}{CH}-CH_2-O)_p CH_2\underset{\underset{O}{\diagdown\diagup}}{CH}-CH_2 \qquad (1\text{-}H)$$

wherein $R_1$ is as defined in the formula 1-A and p is 0 or a positive integer of 1–3.

Of those compounds of (1)–(8) above, hydroxy- or epoxy-containing ones represented by the formulae 1-A, 1-C, 1-D, 1-E, 1-F and 1-H are particularly preferred.

A-II. Preferred as the acrylamide derivatives or methacrylamide derivatives possessing at least one group selected from the group consisting of carboxyl group, epoxy group, amino group and hydroxyl group, in which are used in the present invention are those which are represented by following formula (2):

$$(Y)_m-X-\underset{\underset{R_4}{|}}{N}-\overset{O}{\overset{\|}{C}}-\overset{R_1}{\underset{|}{C}}=CH_2 \qquad (2)$$

wherein m is 1 or 2, $R_1$ is a hydrogen atom or a methyl group, $R_4$ is a hydrogen atom or a $C_{1-10}$ hydrocarbon residue, Y is $$-OH,\ -NH_2,\ -\underset{\underset{O}{\diagdown\diagup}}{CH}-CH_2,\ -\overset{O}{\overset{\|}{OP}}(OH)_2$$

or $-COOH$ and

X is a $C_{1-25}$ organic group of $(m+1)$ valence.

Of the compounds represented by the above formula (2), those in which Y is a carboxyl group or a hydroxyl group are particularly preferred.

As such compounds the following are particularly preferred:

(9) Compounds represented by following formula (2-A):

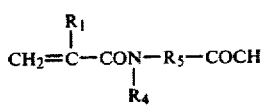

(2-A)

wherein $R_4$ is a hydrogen atom or a $C_{1-3}$ alkyl or phenyl group, $R_5$ is a straight chain or branched $C_{1-6}$ hydrocarbon residue and $R_1$ is as defined in the formula (1) and formula (2).

(10) Compounds represented by following formula (2-B):

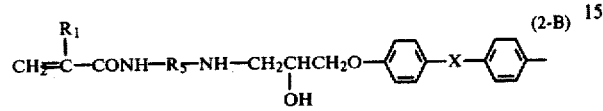

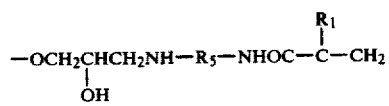

wherein $R_1$ and X are as defined in the formula 1-D and $R_5$ is as defined in the formula 2-A. Of the above-illustrated compounds (1)–(10), in general, acrylate or methacrylate esters are more preferred than acrylamide derivatives of (9) or (10).

The following are specific preferred examples of those compounds represented by the formulae 1-A to 1-H and formulae 2-A and 2-B.

For formula 1-A:

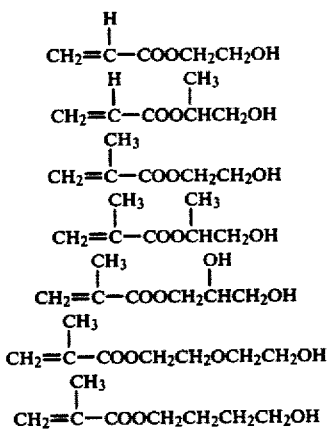

1.
2.
3.
4.
5.
6.
7.

For formula 1-B:

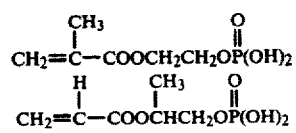

8.
9.

For formula 1-C:

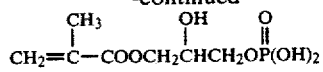
10.

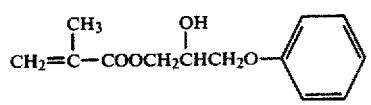
11.
12.
13.

For formula 1-D:

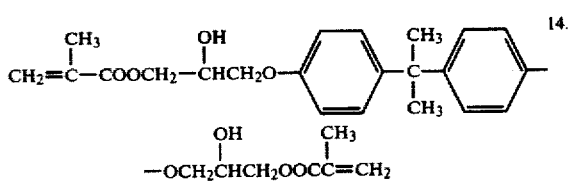
14.

For formula 1-E:

15.

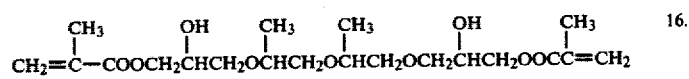
16.

For formula 1-F:

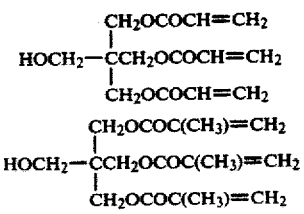
17.
18.

For formula 1-G:

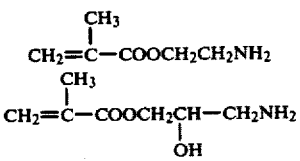
19.
20.

For formula 1-H:

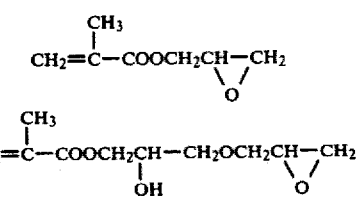
21.
22.

-continued

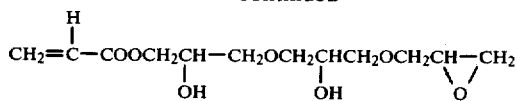
23.

For formula 2-A:

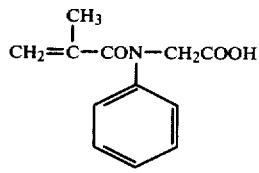
24.

For formula 2-B:

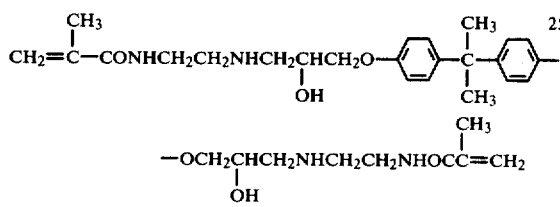
25.

For others:

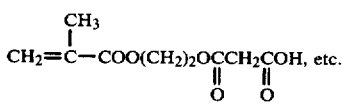
26.

In the next place, explanations will be given of the alkoxy-containing titanium compounds and alkoxy-containing silicon compounds used as the component B in the present invention.

B-I. Preferred as the alkoxy-containing titanium compounds are those compounds which are represented by following formula (3):

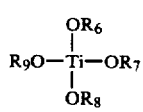  (3)

wherein $R_6$ is a $C_{1-20}$ aliphatic hydrocarbon residue which may optionally possess one or two hydroxyl groups, a $C_{1-3}$ alkoxy group or di(hydroxyalkyl)amino group (wherein the alkyl group has the carbon number of 2 or 3) and $R_7$, $R_8$ and $R_9$ may be each or mutually identical with or different from $R_6$ and stand for a hydrocarbon residue which may possess the same substituents as those of $R_6$, or a group represented by following formula (3'):

  (3')

wherein $R_{10}$ is an olefinic hydrocarbon residue represented by formula

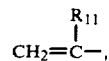

wherein $R_{11}$ is a hydrogen atom or a methyl group, or a $C_{1-20}$ saturated aliphatic hydrocarbon residue and said saturated hydrocarbon residue may optionally possess 1 or 2 hydroxyl groups (—OH), alkoxy group (with the carbon number of 1-3) or acyl group represented by formula

(wherein $R_{21}$, is an alkyl group with the carbon number of 1-3).

The following are particularly preferred examples of the titanium compounds represented by the formula (3) above:

(11) Compounds represented by following formula (3-A):

  (3-A)

wherein $R_{6a}$, $R_{6b}$, $R_{6c}$ and $R_{6d}$ may be each identical or different and stands for a $C_{1-20}$ aliphatic hydrocarbon residue which may possess, as substituent, 1 or 2 hydroxyl groups, a $C_{1-3}$ alkoxy group or di(hydroxyethyl)amino group.

(12) Compounds represented by following formula (3-B):

  (3-B)

wherein f is 1, 2 or 3, $R_{6a}$ is as defined in the formula 3-A, $R_{7a}$ is a $C_{1-20}$ saturated aliphatic hydrocarbon residue and said saturated hydrocarbon residue may possess 1 or 2 hydroxyl groups, a $C_{1-3}$ alkoxy group or $C_{1-3}$ acyl group.

(13) Compounds represented by following formula (3-C):

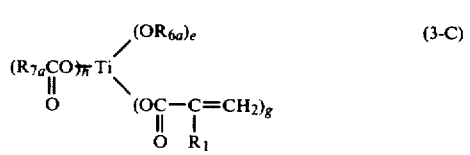  (3-C)

wherein e, g and h are each 1 or 2 and a sum of e, g and h is 4 and $R_{6a}$ and $R_{7a}$ are as defined in the formula 3-B and $R_1$ is a hydrogen atom or a methyl group.

Of these compounds it is tetraalkoxy titanium represented by the formula 3-A that is particularly advantageous.

B-II. As the alkoxy-containing silicon compounds capable of being used as the component B, silicon-containing organic compounds possessing at least three alkoxy groups are preferred.

The following are particularly preferred ones:

(14) Compounds represented by the following formula (4-A):

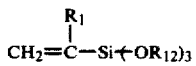
(4-A)

wherein $R_1$ is a hydrogen atom or a methyl group and $R_{12}$ is a $C_{1-4}$ alkyl group and said alkyl group may possess, as substituent, a $C_{1-2}$ alkoxy group.

(15) Compounds represented by following formula (4-B):

(4-B)

wherein $R_{12}$ is as defined in the formula 4-A and $R_{13}$ is a straight chain or branched $C_{2-6}$ divalent aliphatic hydrocarbon residue.

(16) Compounds represented by following formula (4-C):

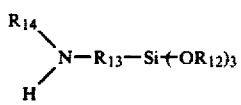
(4-C)

wherein $R_{12}$ and $R_{13}$ are as defined in the formula 4-B and $R_{14}$ is a $C_{1-5}$ ω-aminoalkyl group.

(17) Compounds represented by following formula (4-D):

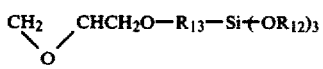
(4-D)

wherein $R_{12}$ and $R_{13}$ are as defined in the formula 4-B.

(18) Compounds represented by following formula (4-E):

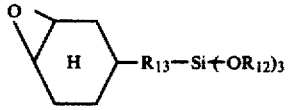
(4-E)

wherein $R_{12}$ and $R_{13}$ are as defined in the formula 4-B.

Of these compounds preferred are silicon-containing organic compounds possessing one olefinic or acrylic unsaturated group and at least three alkoxy groups as represented by the said formulae 4-A and 4-B.

The following are specific preferred examples of the above-described component B:

For formula 3A:

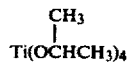
27.

$Ti(OCH_2CH_2CH_2CH_3)_4$    28.

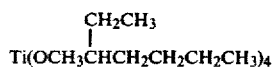
29.

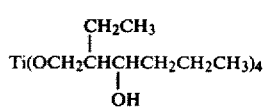
30.

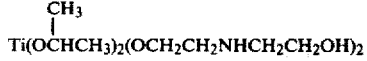
31.

32. $Ti(OC_{18}H_{37})_4$

For formula 3B:

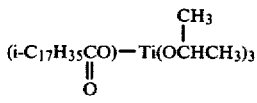
33.

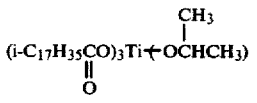
34.

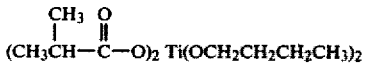
35.

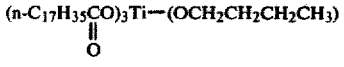
36.

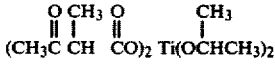
37.

For formula 3C:

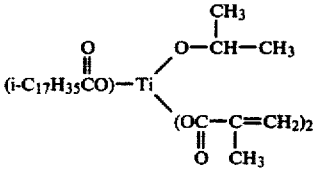
38.

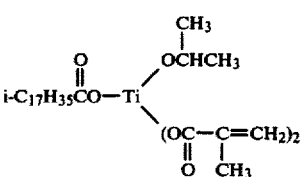
39.

For formula 4A:

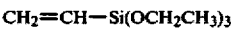
40.

41.

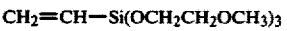
42.

For formula 4B:

43.

44.

-continued

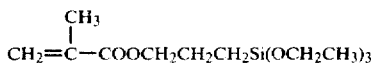
45.

For formula 4C:
46. $NH_2-CH_2CH_2CH_2Si(OCH_2CH_3)_3$
47. $NH_2CH_2CH_2NHCH_2CH_2CH_2Si(OCH_3)_3$ For formula 4D:

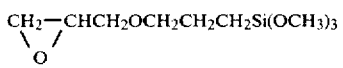
48.

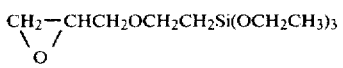
49.

For formula 4E:

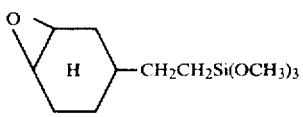
50.

51.

30–99.8% by weight of component A and 70–0.2% by weight of component B will suffice for the bonding composition of the present invention, but those which comprise 50–99.5% by weight of component A and 0.5–50% by weight of component B are preferred.

In the present invention, in the case of component B being titanium compound, those which comprise 80–99.5% by weight, and 95–99.5% by weight, in particular, of component A and 0.5–20% by weight, and 0.5–5% by weight, in particular, of component B, are preferred. In the case, further, of component B being silicon compound, proportions in which the said composition are compounded can vary in a considerably wide range, but those which comprise 50–95% by weight of component A and 5–50% by weight of component B are preferred. Even if acrylate esters and/or methacrylate esters, component A, are to be used alone as bonding material, there can be obtained a certain degree of bondability to the hard tissue of the human body, but 0.5% by weight or more of organometallic compound, component B, is needed for the achievement of the purpose of the present invention and if on the contrary, the component B is mixed in as great an amount as to exceed 50% by weight, the strength of the cured film of the bonding composition will be lowered and in the case, for instance, of using the said composition as bonding agent between the hard tissue of the human body and the restorative filling material, the bonding strength between the both tends to be lowered.

Particulars remain unknown of the chemical reaction mechanism for explaining the reason why an extremely excellent bonding effect is obtained when the bonding compositions of the present invention are applied to the hard tissue of the human body for causing the bonding to the hard tissue of an operative dentistry and prosthetic dentistry material, but it is considered due to the fact that the content of preferably 50–99.5% by weight of hydrophilic acrylate or methacrylate monomer in the composition of the present invention results in good wetting on the surface of the hard tissue and uniform coating of even irregular portions of the hard tissue surfaces and besides, an intensified chemical bonding force with the hydrophilic part contained in the resin components on the hard tissue surface and the operative dentistry and prosthetic dentistry material and formation of a steadfast high polymer film between the hard tissue surface and the operative dentistry and prosthetic dentistry material and that with alkoxy-containing organometallic compound (component B) preferably contained in the amount of 0.5–50% by weight, the alkoxy group of the metal compound reacts with trace water or water film constituting a factor impeding the bondability between the operative dentistry and prosthetic dentistry material remaining on the hard tissue surface and the hard tissue surface, whereby to remove the trace water or water film out of the system and simultaneously the alkoxy group reacts with the trace water or water film and is transformed into a hydroxy group whereby to bond steadfastly to the hydrophilic group present on the hard tissue surface.

In the case, in particular, of the component B being a titanium compound, because of the very high reactivity of the alkoxy group with the trace water or water film left over on the hard tissue surface, the bonding effect to the hard tissue clearly exhibits itself even with a small amount of the titanium compound component in the composition belonging to the present invention. On the contrary, if the titanium compound component is too high, the permanent bondability in the wet condition may sometimes be lowered. It is conceived, as mentioned above, that relatively small amounts will suffice for the amount of the titanium compound mixed in the composition.

The bonding compositions of the present invention for the hard tissue of the human body contain, in practical use, usually a catalyst for the polymerization of the composition and an activator for the formation of free radicals by the reaction with the catalyst besides the said composition.

For a method of using such bonding material it is very convenient to prepare in advance a solution comprising the said composition and an activator (solution A) and a solution comprising the said composition and a catalyst (solution B), for instance, since the polymerization of the said composition is begun upon mixing these two kinds of solutions when used by doctors.

The bonding composition of the present invention can readily be polymerized and cured by use of the catalyst and the activator.

On this occasion, the application of heat often does harm to the human body when used in the fields associated with the human body and hence, preferred are those compositions which can be cured at normal temperature when used.

In practical use, the bonding agent of the present invention should advantageously be formulated in a two-liquid type agent, one containing a catalyst and the other containing an activator, for use by mixing both of them together immediately before use.

As the catalyst, a peroxide is preferred and preferably it should be used in combination with an activator. As the peroxide catalyst there can be cited, for instance, diacyl peroxides, such as benzoyl peroxide, parachlorobenzoyl peroxide, 2,4-dichlorobenzoyl peroxide, acetyl peroxide, lauroyl peroxide and so on, hydroperoxides, such as tertiary butyl hydroperoxide, cumene hydroperoxide, 2,5-dimethylhexane-2,5-dihydroperoxide and so on, ketone peroxides, such as methyl ethyl ketone peroxide and so on, peroxycarbonates, such as tertiary butyl peroxybenzoate and so on, etc.

These peroxide catalysts should preferably be used in proportions of 0.1–3.5% by weight based on the total weight of the polymerizable monomer of the present invention represented by the said formula (II) or (III).

As the activator capable of use in combination with the peroxide can be cited, for instance, tertiary amines, such as N,N-bis-(2-hydroxyethyl)-4-methylaniline, N,N-bis-(2-hydroxyethyl)-3,4-dimethylaniline, N,N-bis-(2-hydroxyethyl)-3,5-dimethylaniline, N-methyl-N-(2-hydroxyethyl)-4-methylaniline, 4-methylaniline, N,N-dimethyl-p-toluidine, N,N-dimethylaniline, triethanolamine and so on, and besides, transition metal ions, such as cobalt naphthenate, cobalt octanate and so on, amine salts of p-toluenesulphonic acids and sulphinic acids and so forth.

These activators can be generally used in proportions of 0.1 to 3.5% by weight based on the total weight of the said polymerizable monomer.

The bonding compositions of the present invention have steadfast and durable bonding strength to the hard tissue of the human body. Not only that, but also they bring about steadfast and durable bonding strength between the operative dentistry and prosthetic dentistry material for the hard tissue of the human body and the hard tissue of the human body.

The bonding compositions of the present invention can be used in combination with any conventionally known resin-forming material or composite resin suitable for medical or dental use.

When using the bonding compositions of the present invention on the occasion of filling teeth with the composite resin for dental use which conventionally had hardly bonding strength to tooth, excellent bonding strength is obtained and cavity sealability can be markedly improved.

Typical of conventionally known resin-forming monomers for medical or dental use and composite resins using such monomers are disclosed, for instance, in the United Stated Patents, British Patents and Japanese Laid-Open Patent Applications (JAPAN KOKAI) which follow:

U.S. Pat. Nos. 3,541,068; 3,597,389; 3,810,938; 3,923,740; 4,067,853; 3,825,518; 3,862,920 and 3,853,962, British Pat. No. 1,451,262, Japanese Laid-Open Patent Applications (JAPAN KOKAI): JAPAN KOKAI No. 48-90332 and JAPAN KOKAI No. 50-116581.

Particulars are given in the co-pending Patent Application Specification of the instant inventors claiming the same priority date as that of the present application, namely, U.S. Ser. No. 138,814, filed Apr. 9, 1980.

The instant inventors found that at least one compound represented by following formula (I):

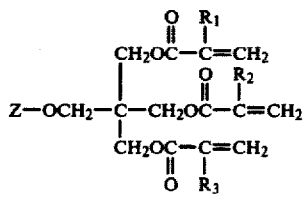

wherein

Z stands for a hydrogen atom or a group represented by following formula:

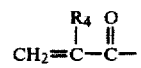

and $R_1$, $R_2$, $R_3$ and $R_4$ may be each identical or different and stand for a hydrogen atom, methyl group, ethyl group or n- or iso-propyl group,
are extremely excellent as a resin-forming monomer for medical or dental use. Conventionally, as filler for the said composite resin are known many inorganic fillers, such as powdered quartz, powdered glass, glass beads, aluminum oxide, borosilicate glass, barium glass, hydroxy apatite, alumino silicate and so on, but the instant inventors found that fillers comprising nitride of at least one member of metal selected from the group consisting of Group IVB, Group VB and Group VIB in the Periodic Table of elements and boron, aluminum and silicon and having a Mohs' hardness of at least 7 and fillers in powder form with particle size of 50 microns or less, in particular, are extremely excellent as the composite resin-forming filler. Particulars of this discovery are given in the said co-pending Patent Application Specification of the instant inventors, namely, U.S. Ser. No. 138,814, filed Apr. 9, 1980.

The bonding compositions of the present invention can be used when filling teeth with the novel composition resin comprising the resin-forming monomer for medical or dental use of the formula (I) by the invention of the instant inventors or such a monomer incorporated with the conventionally known inorganic filler or the said metal nitride filler belonging to the invention of the instant inventors. In this case, the novel composite resin equals dental amalgam in physical properties, such as compressive strength, hardness, abrasion resistance and so on, and in addition, the bonding strength to teeth is markedly improved and hence, the present invention could provide quite novel dental material as the restorative filling material for molar for which dental amalgam alone was conventionally available.

Making the most of the excellent bonding to the hard tissue of the human body, the bonding compositions of the present invention are applicable to bone cement, artificial bond and so forth in the orthopedic and restorative surgery field, or restorative material for crown bridge, core material for crown, dental cement, filling material, pit and fissure sealant and so forth in the operative dentistry and prosthetic dentistry field.

The present invention will be specifically explained with the reference to working examples as follows. Unless otherwise specified, "part" and "%" in the working examples mean "part by weight" and "% by weight".

In this connection, in the working examples the method for the measurement of bonding test and percolation follows the hereinafter-described procedure.

[Method of bonding test]

The crown of a fresh anterior bovine tooth implanted in an acryl resin square rod was horizontally ground until the enamel was exposed. It was stored in water and taken out from the water immediately before the bonding test was conducted. Water on the surface was wiped off, the enamel was etched with 50% aqueous phosphate solution for one minute and all specimens were dried with air.

Next, the tooth surface was coated with the bonding composition and then curable resin and a great deal of inorganic filler-based composite resin was placed on the surface of the bovine enamel, an acryl square rod was stuck and slowly pressed against the enamel from above, left to stand at room temperature for 15 minutes and then immersed into water at 37° C. for 24 hours. Both ends of the acryl square rod of the specimen taken out were pulled apart to determine its bonding strength. Bonding strength was indicated by the average values for 10 testpieces.

In the Examples the method of testing the marginary seal followed the hereinbelow-described procedure.

[Method of percolation test]

The surface of a fresh sound human tooth was fully cleaned. After forming 4 each of simple cylindrical cavities of about 35 mm across and 2 mm deep, reaching the dentin, for every sample tooth they were stored by immersing same into physiological saline solution. The extracted tooth taken out from the physiological saline solution immediately prior to the instant test was cleansed with distilled water, then cleaned with ethanol and dried. After that, the enamel in the cavity alone was etched with 40% $H_3PO_4$ for one minute, then cleansed with water and dried. Then, optional bonding composition was coated on the cavity surface and it was filled with optional composite resin and pressed with polyester strips until it was cured. After curing, it was immersed into artificial saliva and left to stand for 14 days. After that, the apical foramen of the tooth was closed with ionomer cement and then immersed alternately for one minute into water heated to 60° C. and 0.2% aqueous fuchsin solution cooled to 4° C. This operation was repeated 120 times.

After passing through this course, the fuchsin adhered to the tooth surface was washed out with water and then the filled portion was cut off longitudinally by means of a diamond disk and the degree in which fuchsin penetrated from the cavity margin was microscopically observed. On that occasion, the ratio of the length of the fuchsin penetration to the length of the cavity wall perpendicular to the tooth surface was assessed as the degree of fuchsin penetration.

EXAMPLE 1

Twelve (12) kinds of bonding compositions as shown in Table 1 were prepared. In the respective cases, the bonding compositions are comprised predominantly of 98 parts of various monomers corresponding to the component A of the present invention mentioned in Table 1 and 2 parts of tetraisopropyl titanate corresponding to the component B of the present invention, but they are of the two liquid type so that they can be cured at room temperature when used. One (solution a) is incorporated with N,N-bis-(2-hydroxyethyl)-4-methylaniline (hereinafter called DEPT for short), an activator, and one (solution b) is incorporated with benzoyl peroxide (hereinafter called BPO for short), a peroxide catalyst, and 2,5-di-tertiary butyl-4-methylphenol (hereinafter called BHT for short), a storage stabilizer, but the amounts in which the additives, such as catalyst and so on, are mixed are optionally set for the preparation of the composite resins as set forth in Table 1 in such a manner as to set at 3 minutes the time required for holding part of the solution prepared by mixing both solutions a and b at a 1:1 ratio between sheets of cover glass until the cover glass stays immobilized. (Measurement temperature was 24° C.) The following is one specific example (in the case of No. 1 in Table 1).

| Composition | Solution a | Solution b |
|---|---|---|
| 2-Hydroxyethyl acrylate | 98 parts | 98 parts |
| Tetraisopropyl titanate | 2 parts | 2 parts |
| DEPT | 2 parts | — |
| BPO | — | 2 parts |
| BHT | — | 0.1 part |

Nos. 2 to 12 in Table 1 were prepared following the same procedure as the above.

As Control there was used a bonding agent "ADAPTIC" (Code No. 20012) of J & J company.

After various said bonding compositions were coated on the phosphate etched bovine enamel according to the above-described "method of bonding test" Paste a and Paste b of the Bis-GMA type composite resin with the following compositions were mixed at a 1:1 ratio, then it was filled and immersed in water for 24 hours to determine the bonding strength. Results were tabulated in Table 1.

For comparison there were also cited the results obtained in the case of directly bonding the said composite resin to the bovine enamel without coating it with the bonding composition.

Method for the preparation of Bis-GMA type composite resin

| Component | Paste a (parts) | Paste b (parts) |
|---|---|---|
| Bis-GMA | 85 | 85 |
| Triethyleneglycol dimethacrylate | 15 | 15 |
| Silane treated $SiO_2$ powder | 300 | 300 |
| DEPT | 2 | — |
| BPO | — | 2.5 |
| BHT | 0.02 | 0.25 |

TABLE 1

| No. | Component A | (No. in parentheses indicates compound No. illustrated in the text) | Solution a DEPT (part) | Solution b BPO (part) | BHT (part) | Bonding strength to enamel (kg/cm$^2$) |
|---|---|---|---|---|---|---|
| 1 | 2-Hydroxyethyl acrylate | (1) | 2.0 | 2.0 | 0.1 | 90–95 |
| 2 | 2-Hydroxypropyl acrylate | (2) | 2.0 | 2.0 | 0.1 | 90–95 |
| 3 | 2-Hydroxyethyl acrylate | (3) | 2.0 | 2.0 | 0.1 | 95–100 |
| 4 | 2-Hydroxypropyl methacrylate | (4) | 2.0 | 2.0 | 0.1 | 95–100 |
| 5 | 2-Methacryloxyethylamide phosphate | (8) | 6.0 | 4.0 | 0.2 | 70–75 |
| 6 | 3-Phenoxy-2-kydroxypropyl methacrylate | (11) | 3.0 | 3.0 | 0.2 | 70–75 |
| 7 | Bisphenol A diglycidyl | | | | | |

TABLE 1-continued

| No. | Component A | (No. in parentheses indicates compound No. illustrated in the text) | Solution a DEPT (part) | Solution b BPO (part) | BHT (part) | Bonding strength to enamel (kg/cm$^2$) |
|---|---|---|---|---|---|---|
|  | methacrylate | (14) | 2.0 | 2.0 | 0.1 | 70–75 |
| 8 | Ethylglycol diglycidyl methacrylate | (15) | 2.0 | 2.0 | 0.1 | 75–80 |
| 9 | Tetramethylolmethane triacrylate | (5) | 1.5 | 1.5 | 0.1 | 85–90 |
| 10 | Aminoethyl methacrylate | (19) | 3.0 | 3.0 | 0.2 | 60–65 |
| 11 | Glycidyl methacrylate | (21) | 4.0 | 4.0 | 0.2 | 95–100 |
| 12 | N-Acryloyl-N-phenyl glycine | (24) | 6.0 | 1.0 | 0.2 | 60–65 |
| Control 1 | Bonding agent "ADAPTIC" (Code No. 20012) made by J & J company |  |  |  |  | 50–60 |
| Control 2 | — |  |  |  |  | 30–40 |

It is noted from Table 1 that if in improving the bonding to the tooth of the Bis-GMA type composite resin, there are used, as the bonding agent, various compositions consisting predominantly of tetraisopropyl titanate (2 parts) corresponding to the component B of the bonding composition of the present invention and various compounds (98 parts) listed in Table 1 corresponding to the component A of the bonding composition of the present invention, in either case, it is much more effective as compared to the case of directly filling with the composite resin or to the case of conventionally available bonding agents.

It is also noted there that it is those compounds represented by formulas 1-A and 1-H in the text that are particularly preferred for the component A of the bonding composition of the present invention.

EXAMPLE 2

Eleven (11) types of bonding compositions as shown in Table 2 were prepared. In the respective cases, composite resins are comprised predominantly of 98 parts of 2-hydroxyethyl methacrylate corresponding to the component A of the composition of the present invention and 2 parts of various titanium compounds corresponding to the component B of the composition of the present invention listed in Table 2 and they are of the two liquid type as is the case with Example 1 and the amounts in which catalyst and so forth are mixed are suitably selected for the preparation of the bonding compositions.

The following is one specific example (in the case of No. 2 in Table 2).

| Composition | Solution a | Solution b |
|---|---|---|
| 2-Hydroxyethyl methacrylate | 98 parts | 98 parts |
| Tetra-n-butyl titanate | 2 parts | 2 parts |
| DEPT | 2 parts | — |
| BPO | — | 2 parts |
| BHT | — | 0.1 part |

No. 1 and Nos. 3 to 11 were prepared following the same procedure as the above.

As Referential Examples 1 and 2, compositions were prepared following the same procedure as that of Nos. 1–11 by using, as the component B, dimethacrylethylene titanate, a titanium compound not corresponding to the component B of the composition of the present invention and by using 2-hydroxyethyl methacrylate alone.

By using various said bonding compositions their bonding strength was measured following the same procedure as that of Example 1. Results were tabulated in Table 2.

TABLE 2

| No. | Component B | (No. in parentheses indicates compound No. illustrated in the text) | Solution a DEPT (part) | Solution b BPO (part) | BHT (part) | Bonding strength to enamel (kg/cm$^2$) |
|---|---|---|---|---|---|---|
| 1 | Tetraisopropyl titanate | (27) | 2.0 | 2.0 | 0.1 | 95–100 |
| 2 | Tetra-n-butyl titanate | (28) | 2.0 | 2.0 | 0.1 | 95–100 |
| 3 | Tetra-kis-(2-ethylhexyl) titanate | (29) | 2.0 | 2.0 | 0.1 | 90–95 |
| 4 | Tetrastearyl titanate | (32) | 2.0 | 2.0 | 0.1 | 85–90 |
| 5 | Tetraoctylglycol titanate | (30) | 2.0 | 2.0 | 0.1 | 90–95 |
| 6 | Tri-n-butoxymonostearyl titanate | (36) | 2.0 | 2.0 | 0.1 | 85–90 |
| 7 | Isopropyl-tri-i-stearyl titanate | (34) | 2.0 | 2.0 | 0.1 | 80–85 |
| 8 | Di-i-propoxybis-(acetylaceto) titanate | (37) | 2.0 | 2.0 | 0.1 | 80–85 |
| 9 | Isopropyl-di-isostearoyl-di-methacryl titanate | (39) | 1.5 | 1.5 | 0.1 | 65–70 |
| 10 | Isopropyl-di-isostearoyl-di-acryl titanate | (38) | 1.5 | 1.5 | 0.1 | 65–70 |
| 11 | Di-n-butoxy-bis-(triethanolamine) titanate | (31) | 2.0 | 2.0 | 0.1 | 60–70 |
| Referential Example 1 | Dimethacrylethylene titanate |  | 2.5 | 2.5 | 0.1 | 50–60 |
| Referential Example 2 | — |  | 2.0 | 2.0 | 0.1 | 50–60 |

It is noted from Table 2 that if in improving the bonding to the tooth of the Bis-GMA type composite resin, there are used, as the bonding agent, various compositions consisting predominantly of 2-hydroxyethyl methacrylate (98 parts) corresponding to the component A of the bonding composition of the present invention and various titanium compounds (2 parts) corresponding to the component B of the bonding composition of the present invention, mentioned in Table 2 in either case, it is more effective as compared to the case of using the titanium compound not corresponding to the component A of the bonding composition of the present invention or to the case of using 2-hydroxymethyl methacrylate alone. It is also noted there that it is tetralkoxy titanium represented by the formula 3-A in the text that is particularly advantageously used as the titanium compound corresponding to the component B of the bonding composition of the present invention.

EXAMPLE 3

There were used, as the bonding composition, those in which the ratio between glycidyl methacrylate corresponding to the component A of the composition of the present invention and tetraisopropyl titanate corresponding to the component B of the composition of the present invention was altered as shown in Table 3, but for the amounts in which additives, such as catalyst and so on, were used on that occasion they were prepared as shown in Table 3 by following the same procedure as set forth in Example 1. By using various said bonding compositions, the bonding strength was measured following the same procedure as that of Example 1. Results were tabulated in Table 3.

TABLE 3

| No. | Glycidyl methacrylate (part) | Tetraisopropyl titanate (part) | Solution a DEPT (part) | Solution b BPO (part) | BHT (part) | Bonding strength to enamel (kg/cm²) |
|---|---|---|---|---|---|---|
| 1 | 100 | 0 | 4.0 | 4.0 | 0.2 | 60–70 |
| 2 | 99.9 | 0.1 | 4.0 | 4.0 | 0.2 | 60–70 |
| 3 | 99.5 | 0.5 | 4.0 | 4.0 | 0.2 | 90–100 |
| 4 | 99.0 | 1.0 | 4.0 | 4.0 | 0.2 | 95–100 |
| 5 | 95.0 | 5.0 | 4.5 | 4.5 | 0.2 | 95–100 |
| 6 | 90 | 10 | 5.0 | 5.0 | 0.2 | 90–100 |
| 7 | 80 | 20 | 6.0 | 6.0 | 0.2 | 80–90 |
| 8 | 50 | 50 | 7.0 | 7.0 | 0.2 | 70–80 |

It is noted from Table 3 that the bonding strength between the composite resin and the tooth is particularly excellent when using, as the bonding agent, those compositions in which the composition ratio between glycidyl methacrylate and tetraisopropyl titanate falls within the specified range, viz., proportions of tetraisopropyl titanate incorporated fall in the range of 0.5–20%.

EXAMPLE 4

Bonding strength was measured by following the same procedure as that of Example 1, using 2-hydroxyethyl methacrylate and vinyl(β-methoxy-ethoxy)silane respectively instead of glycidyl methacrylate and tetraisopropyl titanate of Example 3 and besides, using various bonding compositions in the same manner as that of Example 3. Results are tabulated in Table 4.

TABLE 4

| No. | 2-Hydroxyethyl methacrylate (part) | Vinyl (β-methoxy-ethoxy) silane (part) | Solution a DEPT (part) | Solution b BPO (part) | BHT (part) | Bonding strength to enamel (kg/cm²) |
|---|---|---|---|---|---|---|
| 1 | 100 | 0 | 2.0 | 2.0 | 0.1 | 50–60 |
| 2 | 99.5 | 0.5 | 2.0 | 2.0 | 0.1 | 60–65 |
| 3 | 95 | 5 | 2.5 | 2.5 | 0.2 | 70–80 |
| 4 | 90 | 10 | 3.0 | 3.0 | 0.2 | 90–95 |
| 5 | 80 | 20 | 4.0 | 4.0 | 0.2 | 95–100 |
| 6 | 50 | 50 | 6.0 | 6.0 | 0.3 | 80–90 |

It is noted from Table 4 that the bonding strength between the composite resin and the tooth is particularly excellent when using, as the bonding agent, those compositions in which the composition ratio between 2-hydroxyethyl methacrylate and vinyl(β-methoxyethoxy)silane falls within the specified range, and more particularly, proportions in which vinyl(β-methoxyethoxy)silane incorporated fall in the range of 5–50%.

EXAMPLE 5

Seven (7) types of bonding compositions as shown in Table 5 were prepared and used. In the respective cases, various compositions consisting predominantly of 80 parts of glycidyl methacrylate corresponding to the component A of the composition of the present invention and 20 parts of various silane compounds corresponding to the component B of the composition of the present invention were prepared by following the same procedure as that of Example 1. Table 5 shows amounts of additives, such as catalyst and so on, incorporated in the respective cases.

The following is one specific example (in the case of No. 1 in Table 5).

| Composition | Solution a | Solution b |
|---|---|---|
| Glycidyl methacrylate | 80 parts | 80 parts |
| γ-Methacryloxypropyl-trimethoxysilane | 20 parts | 20 parts |
| DEPT | 3 parts | — |
| BPO | — | 3 parts |
| BHT | — | 0.2 part |

As referential example the composition in the case of glycidyl methacrylate alone was prepared in the same manner as in the case of No. 1–No. 7. Using various said bonding compositions, the bonding strength was measured by following the same procedure as that of Example 1. Results were tabulated in Table 5.

TABLE 5

| No. | Component B | (No. in parentheses indicates compound No. illustrated in the text) | Solution a DEPT (part) | Solution b BPO (part) | BHT (part) | Bonding strength to enamel (kg/cm$^2$) |
|---|---|---|---|---|---|---|
| 1 | γ-Methacryloxypropyltri methoxysilane | (43) | 3 | 3 | 0.2 | 100–105 |
| 2 | N-β-aminoethyl-γ-aminopropyl tri-methoxysilane | (47) | 5 | 5 | 0.3 | 80–85 |
| 3 | β-(3,4-Epoxycyclohexyl)ethyl tri-methoxysilane | (50) | 5 | 5 | 0.3 | 80–85 |
| 4 | γ-Glycidoxypropyltri- methoxysilane | (48) | 5 | 5 | 0.3 | 85–90 |
| 5 | Vinyltriethoxysilane | (40) | 4 | 4 | 0.2 | 95–100 |
| 6 | γ-Aminopropyltriethoxysilane | (45) | 5 | 5 | 0.3 | 85–90 |
| 7 | Vinyltris-(β-methoxyethoxy) silane | (42) | 4 | 4 | 0.2 | 95–100 |
| Referential Example | — | | 4 | 4 | 0.2 | 60–70 |

It follows from Table 5 that if in improving the bonding to the tooth of the Bis-GMA type composite resin, there are used, as the bonding agent, various compositions consisting predominantly of glycidyl methacrylate (80 parts) corresponding to the component A of the composition of the present invention and various silane compounds (20 parts) corresponding to the component B of the composition of the present invention mentioned in Table 5, in either case, it is much more effective as compared to the case of using no silane compounds.

It is silane compounds represented by the formulas 4-A and 4-B in the text that are particularly advantageously used as the silane compound corresponding to the component B of the bonding composition of the present invention.

EXAMPLE 6

Various bonding compositions used in No. 9 and No. 11 of Example 1, No. 5 of Example 2, No. 5 of Example 4 and No. 1 of Example 5 were used as the bonding agent on the occasion of filling the tooth with following novel composite resins for which the instant inventors enjoy the same priority claim date as in the present application. The method for the preparation of novel composite resin and the method for its filling are identical with the case for the Bis-GMA type composite resin of Example 1. The method for the measurement of its bonding strength to the tooth is identical with that used in Example 1.

Listed together are those results obtained in like manner when using the bonding agent "ADANTIC", a product of J & J company, and when using no bonding agent at all. Results were tabulated in Table 6.

Method for the preparation of novel composite resin

| Component | Paste a (parts) | Paste b (parts) |
|---|---|---|
| Tetramethylolmethane triacrylate | 55 | 55 |
| Tetramethoylolmethane tetracrylate | 45 | 45 |
| Powdered silicon nitride (Si$_3$N$_4$) | 420 | 420 |
| DEPT | 2.0 | — |
| BPO | — | 2.5 |
| BHT | — | 0.15 |

TABLE 6

| No. | Bonding composition | Bonding strength to enamel (kg/cm$^2$) |
|---|---|---|
| 1 | same as used in No. 9 of Example 1 | 100–105 |
| 2 | same as used in No. 11 of Example 1 | 110–120 |
| 3 | same as used in No. 5 of Example 2 | 105–110 |
| 4 | same as used in No. 5 of Example 4 | 105–110 |
| 5 | same as used in No. 1 of Example 5 | 110–120 |
| 6 | Bonding agent "ADAPTIC" made by J & J company | 60–70 |
| Referential Example | not used | 60–70 |

The above results show that the bonding compositions of the present invention are very effective when used as the bonding agent in filling teeth with the said novel composite resin discovered by the instant inventors and show a higher bonding strength than in the case of using in combination with the Bis-GMA type composite resin as noted from comparisons with No. 9 and No. 1 of Example 1, No. 5 of Example 2, No. 5 of Example 4 or No. 1 of Example 5, etc.

EXAMPLE 7

The bonding composition used in No. 11 of Example 1 was coated on the bovine enamel and then it was filled and bonded with the Bis-GMA type composite resin and novel composite resin used in Example 1 and Example 6 and immersed in water at 37° C. for a given time to determine the bonding strength. Investigations were made on the change of the bonding strength with the lapse of time. Results were tabulated in Table 7.

TABLE 7

| Composite resin used | Bonding strength to enamel (kg/cm²) [immersed in water at 37° C.] | | | |
|---|---|---|---|---|
| | After 1 day | After 1 month | After 6 months | After 1 year |
| Bis-GMA type | 95-100 | 95-100 | 90-95 | 85-90 |
| Novel | 110-125 | 110-120 | 105-110 | 100-105 |

It is noted from Table 7 that when using, as the bonding agent, the bonding composition of the present invention in filling the tooth with the said Bis-GMA type composite resin and the said novel composite resin, it is much less in the lowering of the bonding strength even in the case of immersing over a prolonged period of time at such conditions as under water at 37° C.

EXAMPLE 8

By using fresh, extracted, sound, human teeth (2 each of anterior teeth, premolars and molars) the degree of fuchsin penetration was assessed by conducting the following test based on the said "method of percolation test."

On that occasion, the same novel composite resin as that of Example 6 was used as the composite resin and the same composite composition as that of No. 9 of Example 1 was used as the bonding agent.

As the result of this test the number of "n" for the subject of measurement of the degree of fuchsin penetration was 48, but in either case, there was recognized no fuchsin penetrating phenomenon and average degree of fuchsin penetration was 0.

That is, what is implied by this is that by jointly using the novel composite resin discovered by the instant inventors as mentioned in Example 6 and the composition used in No. 9 of Example 1 being the composition of the present invention bonding extremely durable to the environmental temperature changes could be brought about in the interface between the tooth and the filling material.

We claim:

1. A bonding composition consisting essentially of
(A) from 30 to 99.8% by weight of at least one polymerizable monomer selected from the monomer group consisting of acrylate esters, methacrylate esters, acrylamide derivatives and methacrylamide derivatives, wherein all the members of said monomer group contain a carboxyl, epoxy, amino or hydroxyl group in the molecule,
(B) from 70 to 0.2% by weight of at least one member selected from the group consisting of
(B-I) alkoxy-containing titanium compounds having the formula $$\begin{array}{c} OR_6 \\ | \\ R_9O-Ti-OR_7 \\ | \\ OR_8 \end{array}$$

wherein $R_6$ is a $C_{1-20}$ aliphatic hydrocarbon having up to two substituents selected from the group consisting of hydroxyl, $C_{1-3}$ alkoxy and di(hydroxyalkyl)amino in which the alkyl has 2 or 3 carbon atoms, $R_7$, $R_8$ and $R_9$, which are the same or different, have the same meaning as $R_6$ and additionally include a group of the formula $$\begin{array}{c} R_{10}C- \\ \| \\ O \end{array}$$

wherein $R_{10}$ is $$CH_2=CH-, \ CH_2=\overset{CH_3}{\underset{|}{C}}-$$

or $C_{1-20}$ saturated aliphatic hydrocarbon containing up to two substituents selected from the group consisting of hydroxyl, $C_{1-3}$ alkoxy and acyl having the formula $$\begin{array}{c} O \\ \| \\ -CR_{21}, \end{array}$$

wherein $R_{21}$ is alkyl having 1 to 3 carbon atoms, and
(B-II) silane compounds containing at least three alkoxy groups in the molecule,
a catalyst for the polymerization of the composition and an activator for the formation of free radicals by reaction with the catalyst.

2. A bonding composition according to claim 1 which contains 50–99.5% by weight of said component A and 50–0.5% by weight of said component B.

3. A bonding composition according to claim 1 or claim 2 in which said component A is acrylate ester or methacrylate ester having the formula (1):

$$(Y)_{\overline{m}}Z\left[\begin{array}{c} O \ R_1 \\ \| \ | \\ OC-C=CH_2 \end{array}\right]_n \quad (1)$$

wherein
n is a positive integer of 1–3,
m is 1 or 2, $$Y \text{ is } -OH, \ -NH_2, \ -CH\underset{O}{-}CH_2, \ -OP(OH)_2 \text{ or } -COOH,$$

Z is a $C_{1-25}$ organic group having a valence of (n+m) and
$R_1$ is hydrogen or methyl.

4. A bonding composition according to claim 3 in which, in the formula (1), $$Y \text{ is } -OH, \ -NH_2, \ -CH\underset{O}{-}CH_2 \text{ or } -OP(OH)_2.$$

5. A bonding composition according to claim 1 or claim 2 in which said component A is acrylamide derivative or methacrylamide derivative having the formula (2):

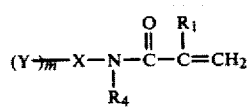 (2)

wherein
m is 1 or 2,
$R_1$ is hydrogen or methyl,
$R_4$ is hydrogen or a $C_{1-10}$ hydrocarbon radical,

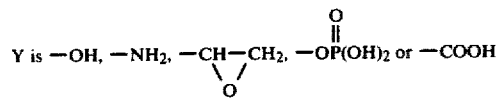

and
X is a $C_{1-25}$ organic group having a valence of $(m+1)$.

6. A bonding composition according to claim 5 in which, in the formula (2), Y is carboxyl or hydroxyl.

7. A bonding composition according to claim 1 or claim 2 in which said silane compound also contains one organic group having, as a terminal group, a mono-olefinic hydrocarbon residue, a primary amino group or an epoxy group.

8. A bonding composition according to claim 1 or claim 2 which contains 80–99.5% by weight of said acrylate esters and/or methacrylate esters as component (A) and 0.5–20% by weight of said titanium compounds (B-I) as component (B).

9. A bonding composition according to claim 1 or claim 2 which contains 50–95% by weight of said acrylate esters and/or methacrylate esters as component (A) and 5–50% by weight of said silane compounds (B-II) as the component (B).

10. A bonding composition according to claim 1 or claim 2 in the form of two packages, one package consisting essentially of a mixture of component A, component B and said polymerization catalyst, the other package consisting essentially of a mixture of component A, component B and said polymerization activator.

11. A bonding composition according to claim 1 or claim 2 in which said silane compound (B-II) has the formula $$D-Si-OR_{12})_3$$

wherein $R_{12}$ is a $C_{1-4}$ alkyl containing up to one $C_{1-2}$ alkoxy group as a substituent, and
D is selected from the group consisting of

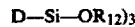 (1)

wherein $R_1$ is hydrogen or methyl

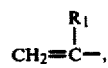 (2)

wherein $R_1$ has the same meaning as defined above and $R_{13}$ is $C_{2-6}$ divalent aliphatic hydrocarbon radical

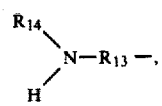 (3)

wherein $R_{13}$ has the same meaning as defined above and $R_{14}$ is $C_{1-5}$ ω-aminoalkyl

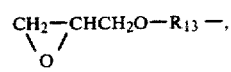 (4)

wherein $R_{13}$ has the same meaning as defined above and

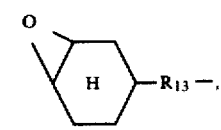 (5)

wherein $R_{13}$ has the same meaning as defined above.

12. A bonding composition according to claim 1 or claim 2 in which component A is selected from the group consisting of
(1) compounds having the formula (1-A):

 (1-A)

wherein
$R_1$ is hydrogen or methyl,
$R_2$ is a straight chain or branched $C_{2-6}$ aliphatic hydrocarbon radical having up to one hydroxyl substituent and
l is 1, 2 or 3,
(2) compounds having the formula (1-B):

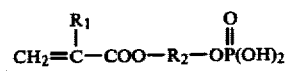 (1-B)

wherein $R_1$ and $R_2$ have the same meanings as defined above provided that when group —$R_2$— possesses —OH as a substituent, this —OH may be a phosphate ester,
(3) compounds having the formula (1-C) and their phosphate esters:

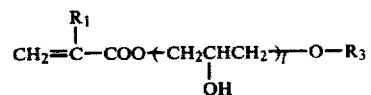 (1-C)

wherein l and $R_1$ have the same meanings as defined above and $R_3$ is $C_{1-3}$ alkyl or phenyl,
(4) compounds having the formula (1-D):

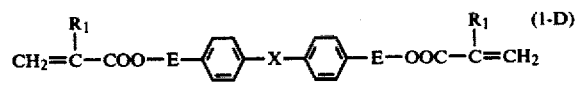 (1-D)

wherein
$R_1$ has the same meaning as defined above,
X is alkylidene or —$SO_2$— and
E is $C_{2-5}$ oxyalkylene having a hydroxyl group as a substituent or alkylidene containing between 1 and 5 carbon atoms with a hydroxyl group as a substituent, (5) compounds having the formula (1-E):

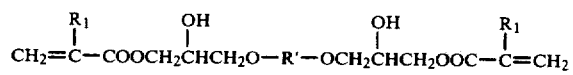
(1-E)

wherein $R_2$ has the same meaning as defined above and R' is

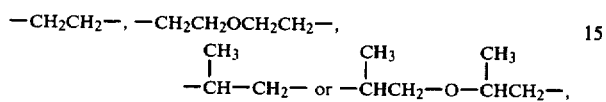

(6) compounds having the formula (1-F):

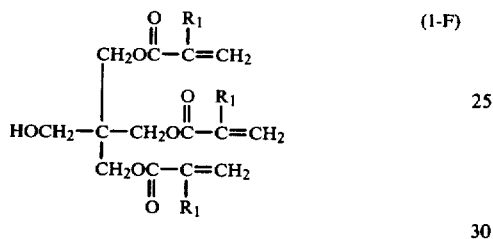
(1-F)

wherein $R_1$ has the same meaning as defined above, (7) compounds having the formula (1-G):

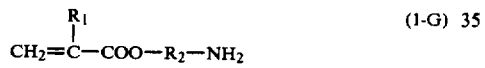
(1-G)

wherein $R_1$ and $R_2$ have the same meanings as defined above, (8) compounds having the formula (1-H):

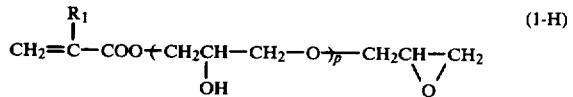
(1-H)

wherein $R_1$ has the same meaning as defined above and p is 0 or a positive integer of 1–3, (9) compounds having the formula (2-A):

(2-A)

wherein $R_4$ is hydrogen atom, $C_{1-3}$ alkyl or phenyl, $R_5$ is a straight chain or branched $C_{1-6}$ hydrocarbon radical and $R_1$ has the same meaning as defined above,

(10) compounds having the formula (2-B):

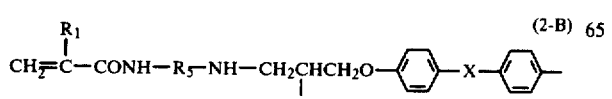
(2-B)

-continued

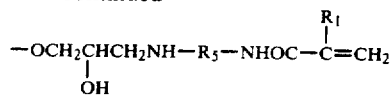

wherein $R_1$, $R_5$ and X have the same meanings as defined above.

13. A bonding composition according to claim 1 or claim 2 in which component A is selected from the group consisting of (1) compounds having the formula

wherein $R_1$ is hydrogen or methyl,

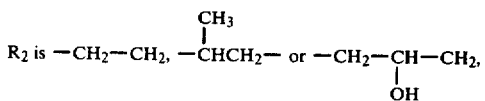

and l is 1, 2 or 3 and (2) compounds having the formula

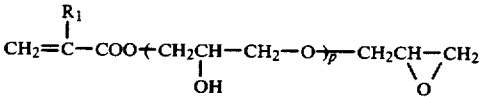

wherein $R_1$ has the same meaning as defined above, and p is zero or an integer of 1–3.

14. A bonding composition according to claim 13 in which component B has the formula

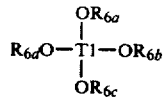

wherein $R_{6a}$, $R_{6b}$, $R_{6c}$ and $R_{6d}$, which are the same or different, are $C_{1-20}$ aliphatic hydrocarbon radicals containing up to 2 substituents selected from the group consisting of hydroxyl, $C_{1-3}$ alkoxy and di(hydroxyethyl)amino.

15. A bonding composition according to claim 13 in which component B is selected from the group consisting of (1) compounds having the formula

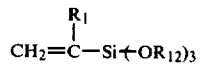

wherein $R_1$ is hydrogen or methyl, and $R_{12}$ is $C_{1-4}$ alkyl containing up to one $C_{1-2}$ alkoxy group, as a substituent, and (2) compounds having the formula

wherein $R_1$ and $R_{12}$ have the same meanings as defined above, and $R_{13}$ is a $C_{2-6}$ divalent hydrocarbon radical.

* * * * *